United States Patent [19]

Alt et al.

[11] 4,284,564

[45] Aug. 18, 1981

[54] PROCESS FOR THE IN-SOLVENT, IN-SITU GENERATION OF HALOALKYL ALKYL ETHERS USEFUL TO PRODUCE N-SUBSTITUTED-2-HALOACETANILIDES

[75] Inventors: Gerhard H. Alt, University City; John P. Chupp, Kirkwood, both of Mo.

[73] Assignee: Monsanto Company, St. Louis, Mo.

[21] Appl. No.: 133,720

[22] Filed: Mar. 25, 1980

[51] Int. Cl.$^3$ .............. C07C 103/375; C07D 305/06; C07D 307/06; C07D 309/04
[52] U.S. Cl. .............. 260/333; 260/345.7 R; 260/347.3; 564/211; 564/214
[58] Field of Search ............ 260/333, 345.7 R, 347.3; 564/211, 214

[56] References Cited

U.S. PATENT DOCUMENTS

| | | | |
|---|---|---|---|
| 2,863,752 | 12/1958 | Hamm et al. | 564/214 X |
| 3,442,945 | 5/1969 | Olin | 564/214 |
| 3,937,730 | 2/1976 | Vogel et al. | 564/214 |
| 3,952,056 | 4/1976 | Vogel et al. | 564/214 |
| 4,070,179 | 1/1978 | Vogel et al. | 564/214 X |
| 4,160,660 | 7/1979 | Vogel et al. | 564/214 X |
| 4,168,965 | 9/1979 | Vogel et al. | 564/214 X |
| 4,200,451 | 4/1980 | Vogel et al. | 564/214 X |

FOREIGN PATENT DOCUMENTS 1008851  11/1965  United Kingdom ..................... 564/214

OTHER PUBLICATIONS

Hubele, CA 90:87084k, (1979).
Monsanto Co., CA 67:99832r, (1967).

Primary Examiner—Thomas A. Waltz
Attorney, Agent, or Firm—Patricia A. Coburn; Donald W. Peterson

[57] ABSTRACT

The present invention is directed to a process for the preparation of certain N-substituted-2-haloacetanilides via the reaction of a secondary 2-haloacetanilide with a haloalkyl ether, particularly, halomethyl ethers, which comprises forming the ether in situ by the in-solvent reaction of an alcohol, formaldehyde or other aldehyde and an acid halide to produce high purity haloalkyl ethers, while decreasing the concentration of undesirable bis by products, as for example bis(chloromethyl) ether. The ether formed in situ thereafter reacts with the secondary 2-haloacetanilide in the presence of a phase transfer catalyst and base to form the N-substituted-2-haloacetanilide.

12 Claims, No Drawings

PROCESS FOR THE IN-SOLVENT, IN-SITU GENERATION OF HALOALKYL ALKYL ETHERS USEFUL TO PRODUCE N-SUBSTITUTED-2-HALOACETANILIDES

BACKGROUND OF THE INVENTION

Although there are a variety of methods known in the art to produce chloromethyl methyl ether (see e.g. U.S. Pat. No. 3,972,947 and U.S. Pat. No. 3,833,602) and it is known to produce 3-haloalkyl halomethyl ether (see U.S. Pat. No. 2,916,522) these methods have inherent disadvantages and often require several manipulative steps which results in an increased cost of the process. Thus, a simple method of producing haloalkyl ethers in high yield which may be used without separation, while decreasing the concentration of undesirable bis(haloalkyl) ethers and especially bis(chloromethyl) ether is highly desirable.

DESCRIPTION OF THE INVENTION

In one aspect, the present relates to an in solvent, in situ process for preparing haloalkyl ethers having the formula $$R_1CHOR \atop X \qquad (I)$$

where $R_1$ is hydrogen or alkyl containing 1 to 4 carbon atoms; X is chloro, bromo or iodo; R is alkyl containing 1 to 10 carbon atoms, alkenyl containing 3 to 10 carbon atoms, cycloalkyl containing 3 to 10 carbon atoms, alkynyl containing 3 to 10 carbon atoms, ($C_{1-5}$) alkoxy ($C_{2-5}$) alkyl, mono-halo ($C_{2-5}$) alkyl, mono-halo ($C_{3-5}$) alkenyl or

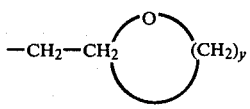

where y is the integer 2, 3, or 4, with the proviso that when R is alkenyl or alkynyl the carbon atom attached to the oxygen atom may not share a double or triple bond with an adjacent carbon atom; which comprises reacting an alcohol of the formula $$ROH \qquad (II)$$

(where R is as defined above) with an aldehyde of formula

(where $R_1$ is as defined above) in the presence of an acid halide and in the presence of a solvent.

The above described reaction may be schematically illustrated as:

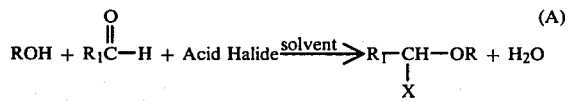

The term "acid halide" as used herein, refers to agents which are capable of liberating a halide ion in situ; such agents are for the purposes of this invention, compounds of the formula $$HX$$

where X is chloro, bromo or iodo, or compounds of the formula

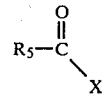

where X is as defined above and $R_5$ is $C_{1-5}$ alkyl, phenyl, benzyl or substituted derivatives thereof. Inorganic halogenating agents such as thionyl chloride, thionyl bromide, sulfuryl chloride, sulfuryl bromide, phosphorous trichloride, phosphorus pentachloride, and the like may also be used.

The preferred acid halides for use herein are HCl, HBr, HI,

especially preferred is

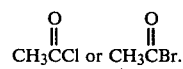

When acetyl chloride or acetyl bromide is employed as the "acid halide" the corresponding methyl acetate produced is compatable with the desired haloalkyl ether product, such that it is not necessary to separate the haloalkyl ether from the methyl acetate, thus avoiding excessive handling of the toxic ethers. If desired, the haloalkyl ether may be separated from the ether product by distillation procedures well known in the art.

The term "alkyl" includes both straight chain and branched chain alkyl groups such as methyl, ethyl, n-propyl, isopropyl, n-butyl, isobutyl, sec-butyl, tert-butyl, n-pentyl, isopentyl, n-hexyl, sec.-hexyl, n-heptyl, n-oxtyl, n-nonyl, n-decyl and the like. Unless otherwise indicated, preferred for use herein are straight chain and branched chain alkyl groups containing 1 to 5 carbon atoms.

The term "alkenyl" refers to both straight chain and branched chain alkenyl groups containing 3 to 10 carbon atoms of the type $-C_nH_{2n-1}$, e.g., $-CH_2-CH=CH_2$, $-CH_2CH_2CH=CH_2$,

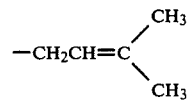

and the like; preferred for use herein are those alkenyl groups containing 3 to 5 carbon atoms.

$C_{3-10}$ Cycloalkyl refers to a monocyclic, saturated hydrocarbon radical, and includes, for example, cyclopropyl, cyclobutyl, cyclopentyl, cyclohexyl, cyclooctyl and the like.

The term "alkynyl" refers herein to a group of the type $-C_nH_{2n-3}$ containing 3 to 10 carbon atoms and includes both straight chain and branched chain groups such as $-CH_2C\equiv CH$, $-CH_2CH_2C\equiv CH$,

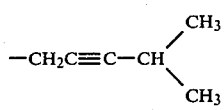

and the like. Preferred for use herein are alkynyl groups containing 3 to 5 carbon atoms.

The term "alkoxyalkyl" refers to a straight chain alkyl group containing 2 to 5 carbon atoms substituted on the terminal carbon by an alkoxy group containing 1 to 5 carbon atoms, e.g., methoxy, ethoxy, n-propoxy, isopropoxy, n-butoxy, sec.-butoxy, tert-butoxy, n-pentoxy and the like.

The term "mono-haloalkyl" or "mono-haloalkenyl" refers herein to a straight chain alkyl or alkenyl group containing 2 to 5 carbon atoms or 3 to 5 carbon atoms respectively, and substituted by one halogen atom, i.e., chloro, bromo, iodo or fluoro atom, as for example, chloroethyl, bromoethyl, fluoroethyl, chloropropyl, bromopropyl, chlorobutyl, bromobutyl, chloropentyl and the like. The radical

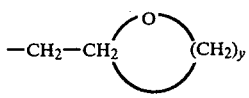

refers to such groups as, for example,

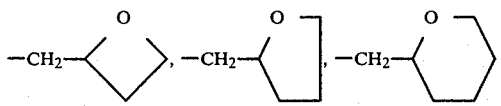

and the like.

In the practice of the process, described herein, a solid, liquid or gaseous form of aldehyde is preferred. Aqueous solutions of aldehyde should be avoided as the presence of water in the reaction tends to inhibit formation of the haloalkyl ether and thus reduce yield. For example, paraformaldehyde or gaseous formaldehyde is preferred to prepare halomethyl ethers.

The above described process employs a solvent which must meet the requirements of being substantially inert to any of the above reactants or products and must possess appropriate solubility for the reactants and products. Suitable solvents include: ethers, for example, ethyl ether, dioxane, tetrahydrofuran, and isopropylether; hydrocarbons, for example, benzene, hexane, cyclohexane, toluene, and chlorinated solvents, for example, methylene chloride, chloroform, dichloroethane, and carbon tetrachloride. The preferred solvent for use in the present invention is methylene chloride.

The presence of solvent in the reaction accomplishes several purposes. In the first instance, the solvent acts to keep the haloalkyl ether in the organic layer and away from the water formed during the reaction. This is desirable since, as previously noted, the yield of high purity haloalkyl ether is reduced by the presence of water in the mixture. The solvent also acts to dilute and thus reduce the concentration of the undesirable bis(-halomethyl) ether by-products formed during the reaction and also provides the reaction medium for the production of the N-substituted-2-haloacetanilide derivatives described below.

As described above, one aspect of the present invention is directed to a process for producting a wide range of haloalkyl ether. Yet another aspect of the present invention is directed to the preparation of certain N-substituted-2-haloacetanilides via a "one pot" or continuous process which comprises the steps of:

(1) Forming a halomethyl ether in situ, in a solvent;
(2) Mixing a secondary 2-haloacetanilide and phase transfer catalyst with the mixture of Step 1; and
(3) Reaction of excess base with the mixture of Step 2.

Specifically, the invention relates to a "one pot", batch or continuous process for preparing a compound of the formula

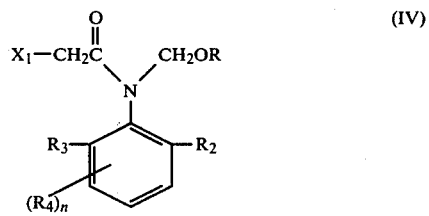

where $X_1$ is chloro, bromo or iodo; R is $C_{1-10}$ alkyl, $C_{3-10}$ alkenyl, $C_{3-10}$ cycloalkyl, $C_{3-10}$ alkynyl, $C_{1-5}$ alkoxy $(C_{2-5})$ alkyl, mon-halo $(C_{2-5})$ alkyl, mono-halo $(C_{3-5})$ alkenyl or

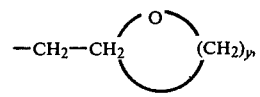

where y is the integer 2, 3, or 4, with the proviso that when R is alkenyl or alkynyl the carbon atom attached to the oxygen atom may not share a double or triple bond with an adjacent carbon atom; $R_2$ is equal to $C_{1-8}$ alkyl, $C_{2-8}$ alkenyl, $C_{3-8}$ alkynyl, $C_{1-8}$ alkoxy, $C_{1-8}$ alkoxy $(C_{1-5})$alkyl, halo $(C_{1-5})$ alkyl, halogen, $NO_2$, $C_{1-5}$ alkoxy $(C_{1-5})$ alkoxy or $C_{1-5}$ alkoxy $(C_{1-5})$ alkoxy $(C_{1-5})$ alkoxy; $R_3$ is equal to hydrogen, $C_{1-8}$ alkyl, $C_{2-8}$ alkenyl, $C_{1-8}$ alkoxy, $C_{1-8}$ alkoxy $(C_{1-5})$ alkyl, halo $(C_{1-5})$ alkyl, halogen or $NO_2$; $R_4$ is equal to $C_{1-8}$ alkyl, halo $(C_{1-5})$ alkyl, halogen or $NO_2$; n is equal to zero, one or two; which comprises reacting, in a solvent and in the presence of a phase transfer catalyst, an alcohol of the formula

ROH   (V)

(where R is as defined in Formula IV above), formaldehyde, an acid halide and a compound of the formula

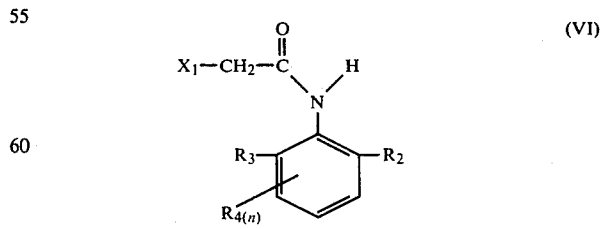

(where $X_1$, $R_2$, $R_3$, $R_4$ and n are as defined in Formula IV above); followed by addition of excess base.

The above reaction may be schematically illustrated as

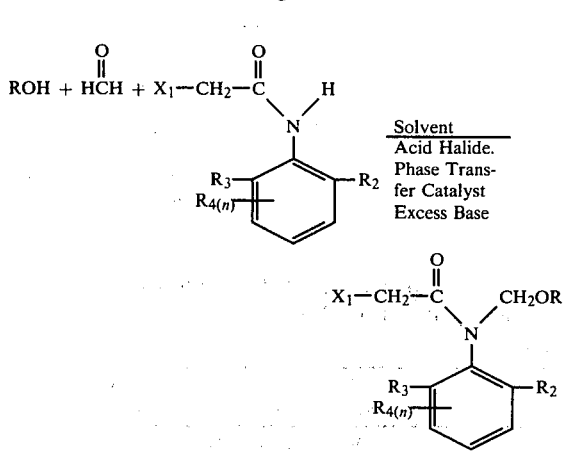

The term "haloalkyl" in Formula IV, used in conjuction with the groups $R_2$, $R_3$ and $R_4$ refers to an alkyl group containing 1 to 5 carbon atoms, such group being substituted by one or more halogen agoms, e.g., chloromethyl, bromoethyl, dichloroethyl, trichloromethyl, trifluoromethyl, pentafluoroethyl, iodomethyl and the like. "Haloalkyl" as used herein specifically includes trifluoromethyl.

In Formula IV above, the terms "$C_{1-5}$ alkoxy ($C_{1-5}$) alkoxy" and "$C_{1-5}$ alkoxy ($C_{1-5}$) alkoxy" includes both straight chain and branched chain alkoxy groups and includes such groups as for example, $-OCH_2OCH_3$, $-OCH_2OC_2H_5$, $-OCH_2CH_2CH_3$, $-OCH_2-OCH_2CH_2-OCH_3$,

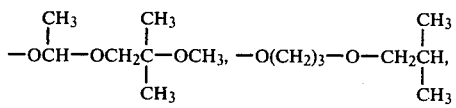

$-(CH_2)_4-O-(CH_2)_3CH_3$ and the like.

The term "base" refers to a base sufficiently strong enough to react with the secondary amide, i.e. the 2-haloacetanilide of Formula VI, to produce incremental concentrations of amide anion.

It will be understood that the weaker the acidity of the amide of Formula VI the stronger must be the base. Thus, e.g. weakly acidic amides such as, e.g., 2'6'-dimethyl-2-chloroacetanilide or 2',6'-diethyl-2-chloroacetanilide require strong bases such as aqueous or solid sodium hydroxide or potassium hydroxide. Further, it is preferred when aqueous caustic is used that the solution be contentrated, i.e. 10–50%. On the other hand, where the amide of Formula VI is strongly acidic, such as, e.g., 2',6'-dinitro-2-chloroacetanilide a weaker base such as solid or aqueous sodium carbonate can be used to successfully generate amide anion.

Bases found to be useful in the above-described process, depending of course on the acidity of the secondary amide of Formula VI are alkali metal hydroxides, carbonates, and phosphates and alkaline earth hydroxides, e.g., calcium oxide or hydroxide, trisodium phosphate, potassium carbonate. The alkali metal hydroxide bases, i.e. NaOH or KOH are preferred for use herein.

Useful phase transfer catalysts for use herein are those containing organic-soluble cations such as those enumerated in U.S. Pat. No. 3,992,432, including ammonium, phosphonium and sulfonium salts. Exemplary phase transfer catalysts include quaternary ammonium salts, e.g., aryl or aralkyl trialkyl ammonium halide salts such as benzyl triethyl ammonium bromide or chloride. Other phase transfer catalysts include the acyclic and cyclic poly ethers which complex with the base cation and then pair with amide anion as couter ion for transport to the organic phase for alkylation. Exemplary of such catalysts would include "18-crown-6" cyclic ether in combination with potassium hydroxide or fluoride as base.

The ratios of reactants in the above described processes are not critical, but are dictated primarily by economic considerations and avoidance of unwanted by-products. Hence, large excesses or deficiencies of any expensive component relative to another component should be avoided. It is preferred however, that an excess of base be used.

The process of this invention may be carried out at temperatures ranging from subzero to ambient or higher, e.g., from $-20°$ to $+100°$ C., but usually room temperatures are sufficient, and desirable. The temperature of the reaction is preferably carried out at from $10°$ to $50°$ C. The process may be carried out under any convenient pressure, either above or below atmospheric.

The process can be carried out either batch wise or continuously. For example, continuous operation the alcohol, aldehyde, acid halide, secondary anilide and phase transfer catalyst maybe introduced into a stream of solvent at a first reaction zone; excess base may thereafter be introduced into the mixture at a second reaction zone located at a point downstream from the first reaction zone.

The following examples illustrate in greater detail the process of this invention wherein an N-substituted 2-haloacetanilide is prepared via the reaction of a secondary 2-haloacetanilide and a halomethyl ether, said ether being formed in situ.

EXAMPLE 1

Preparation of 2'-Methoxy-6'-Methyl-N[(2-methylbutoxy)methyl]-2-chloroacetanilide.

8.8 g. (0.1 moles) of 2-methylbutanol and 1.5 g. (0.05 moles) of paraformaldehyde were added to 100 ml. of methylene chloride and the mixture chilled. To the chilled mixture was added, with stirring, 6.1 g. (0.05 moles) of acetyl bromide. Stirring was continued until all paraformaldehyde dissolved. To this mixture was added 4.7 g. (0.022 moles) of 2'-methoxy,6'-methyl-2-chloroacetanilide and 2.2 g. of phase transfer catalyst in 50 ml. of methylene chloride. Thereafter, 50 ml. of 50% NaOH was added in one portion and the solution was stirred for 5 hours, at which time 100 ml. of cold $H_2O$ was added to facilitate separation of the organic/aqueous layers. The layers were separated and the organic layer was washed once with $H_2O$, dried over $MgSO_4$, evaporated and Kugelohr distilled, 120° C. (0.02 mmHg) to yield 2.2 g. of yellow oil (32% yield) indentified as 2'-methoxy,6'-methyl-N-[(2-methylbutoxy)methyl]-2-chloroacetanilide.

Anal. Calc'd. for $C_{16}H_{24}ClNO_3$: C, 61.24; H, 7.71; Cl, 11.30; Found: C, 61.29; H, 7.76; Cl, 11.35.

In similar fashion the process described above was used to prepare the compounds identified in Table 1 below; said process maybe schematically illustrated as:

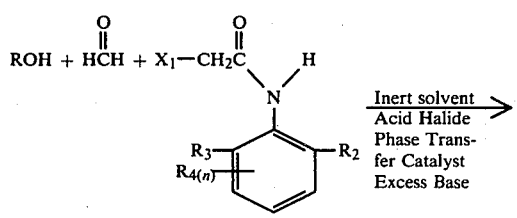

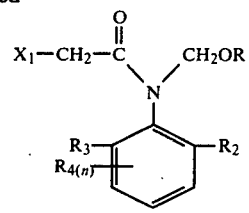

-continued

In the examples shown in Table I below, $X_1$ is equal to chloro and n is equal to zero.

TABLE 1

| Ex. No. | R | $R_2$ | $R_3$ | mp °C. | b.p. °C. | % Yield | Empirical Formula | Analysis | Calc'd | Found |
|---|---|---|---|---|---|---|---|---|---|---|
| 2 | —CH$_2$C≡CH | —OCH$_3$ | —CH$_3$ | 75–76 | — | 54 | C$_{14}$H$_{16}$ClNO$_3$ | C<br>H<br>Cl | 59.68<br>5.72<br>12.58 | 59.58<br>5.76<br>12.53 |
| 3 | —CH$_2$CH$_2$(CH$_2$)$_3$CH$_3$ | —OCH(CH$_3$)$_2$ | —CH$_3$ | — | 120° @ 0.08mmHg | 94 | C$_{18}$H$_{28}$ClNO$_3$ | | | |
| 4 | —CH$_2$C(CH$_3$)$_2$(CH$_2$)$_2$CH$_3$ | —OCH$_3$ | —CH$_3$ | — | 130° @ 0.04mmHg | 78 | C$_{18}$H$_{28}$ClNO$_3$ | C<br>H<br>Cl | 63.24<br>8.26<br>10.37 | 63.55<br>7.80<br>10.50 |
| 5 | —CH$_2$—CH=CHCl | —OCH$_3$ | —CH$_3$ | — | 123° @ 0.03mmHg | 85% | C$_{14}$H$_{17}$Cl$_2$NO$_3$ | C<br>H<br>Cl | 52.85<br>5.39<br>22.28 | 52.79<br>5.44<br>21.79 |
| 6 | —CH$_2$CH$_2$OCH$_3$ | —OC$_2$H$_5$ | —CH(CH$_3$)$_2$ | — | 130° @ 0.04mmHg | 88 | C$_{17}$H$_{26}$ClNO$_4$ | C<br>H<br>Cl | 59.38<br>7.62<br>10.31 | 59.38<br>7.62<br>10.32 |
| 7 | —CH$_2$CH=CH$_2$ | —O(CH$_2$)$_5$CH$_3$ | —CH$_3$ | — | 133° @ 0.03mmHg | 69 | C$_{19}$H$_{28}$ClNO$_3$ | C<br>H<br>Cl | 64.49<br>7.98<br>10.02 | 64.55<br>8.02<br>10.07 |
| 8 | —CH$_2$C(CH$_3$)$_3$ | —OCH$_3$ | —CH$_3$ | — | 105° @ 0.03mmHg | 97 | C$_{16}$H$_{24}$ClNO$_2$ | C<br>H<br>Cl | 61.24<br>7.71<br>11.30 | 61.04<br>7.63<br>11.35 |
| 9 | —CH$_2$CH$_2$Cl | —OCH$_3$ | —CH$_3$ | — | 129° @ 0.05mmHg | 98 | C$_{13}$H$_{17}$Cl$_2$NO$_3$ | C<br>H<br>Cl | —<br>—<br>— | —<br>—<br>— |
| 10 | —CH(CH$_3$)$_2$ | —OCH$_2$CH(CH$_3$)$_2$ | H | — | — | — | C$_{17}$H$_{26}$ClNO$_3$ | C<br>H<br>Cl | 62.28<br>7.99<br>10.87 | 62.41<br>8.04<br>10.70 |
| 11 | —CH$_2$-(tetrahydropyranyl) | —OCH$_3$ | —CH$_3$ | — | 200° @ 0.4mmHg | — | C$_{17}$H$_{24}$ClNO$_4$ | C<br>H<br>Cl | 59.73<br>7.08<br>10.37 | 59.64<br>7.10<br>10.37 |
| 12 | cyclohexyl | —OCH$_3$ | —CH$_3$ | — | 130° C. @ 0.02mmHg | 100 | C$_{16}$H$_{22}$ClNO$_3$ | C<br>H<br>Cl | 61.63<br>7.11<br>11.37 | 61.55<br>7.11<br>11.27 |
| 13 | —CH(CH$_3$)CH$_2$O(CH$_2$)$_2$CH$_3$ | —OCH$_3$ | —CH$_3$ | — | — | — | C$_{17}$H$_{26}$ClNO$_3$ | C<br>H<br>Cl | —<br>—<br>— | —<br>—<br>— |
| 14 | —(CH$_2$)$_2$CH$_3$ | —NO$_2$ | —NO$_2$ | — | — | 93 | C$_{12}$H$_{14}$ClN$_3$O$_6$ | C<br>H<br>N | 43.45<br>4.25<br>12.67 | 43.41<br>5.29<br>12.20 |
| 15 | —C$_2$H$_5$ | —NO$_2$ | —CH$_3$ | 96–98 | — | — | C$_{12}$H$_{15}$ClN$_2$O$_4$ | C<br>H<br>N | 50.27<br>5.27<br>9.77 | 50.27<br>5.27<br>9.75 |
| 16 | —C$_2$H$_5$ | —NO$_2$ | —H | 63–65 | — | 48 | C$_{11}$H$_{13}$ClN$_2$O$_4$ | C<br>H<br>N | 48.45<br>4.81<br>10.27 | 48.51<br>4.82<br>10.25 |
| 17 | —CH$_2$CH(CH$_3$)$_2$ | —NO$_2$ | —H | — | — | 66 | C$_{13}$H$_{17}$ClN$_2$O$_4$ | C<br>H<br>N | 51.92<br>5.70<br>9.31 | 50.62<br>5.83<br>9.21 |
| 18 | —CH$_3$ | —NO$_2$ | —NO$_2$ | 105.5–108 | — | 80 | C$_{10}$C$_{10}$ClN$_2$O$_6$ | C<br>H<br>N | 39.55<br>3.32<br>13.84 | 39.42<br>3.22<br>14.22 |

Example 19 illustrates the use of HCl as the acid halide.

EXAMPLE 19

Preparation of 2'-Methoxy-6'-Methyl-N-(Isorpropoxy)methyl-2-chloroacetanilide.

2.8 g. of isopropanol and 1.5 g. of paraformaldehyde were added to 100 ml. of methylene chloride and the mixture treated with gaseous HCl at room temperature. To this mixture was added 5.0 g. of 2'-methoxy-6'-methyl-2-chloroacetanilide and 2.0 g. of phase transfer catalyst at 25° C. Thereafter, 25 ml. of 50% NaOH was added in one portion and the temperature of the reaction mixture rose to 37° C. The mixture was cooled to 26° C. and stirred for 40 minutes, whereupon GLC showed the reaction complete. 100 ml. of cold $H_2O$ was added to facilitate separation and the organic layer was washed once with $H_2O$, dried over $MgSO_4$, evaporated and Kugelrohr distilled, b.p. 180° C. (0.05 mmHg) to yield an oil identified as 2'-methoxy,6'-methyl-N-(isopropoxy)methyl-2-chloroacetanilide.

Anal. Calc'd. for $C_{13}H_{18}ClNO_3$: C, 57.46; H, 6.68; Cl, 5.51; Found: C, 57.32; H, 6.72; Cl, 5.13.

Example 20 and the examples shown in Table II below, illustrate the preparation of 2-haloacetanilide compounds wherein $R_1$ is $C_{1-5}$ alkoxy($C_{1-5}$) alkoxy or $C_{1-5}$ alkoxy ($C_{1-5}$) alkoxy ($C_{1-5}$) alkoxy.

EXAMPLE 20

Preparation of 2'-[(2-Ethoxy)ethoxy]-6'-Isopropyl-N-(Ethoxy)methyl-2-chloroacetanilide.

A mixture containing ethyl alcohol (5.75 g; 0.125 mole) and paraformaldehyde (1.86 g; 0.062 mole) in 100 ml. of methylene chloride was cooled to 5° C. To the cooled mixture was added acetyl bromide (7.56 g; 0.062 mole) and the resulting mixture was stirred for 45 minutes. To the resulting mixture was added a mixture containing 2-[(2-ethoxy)ethoxy]-6'-isopropyl-2-chloroacetanilide (4.5 g; 0.015 mole), 1.5 g. of benzyltriethylammonium bromide (phase transfer catalyst) in 75 ml. of methylene chloride. While maintaining the temperature of the reaction mixture at 15° C., 45 ml. of a 50% solution of sodium hydroxide was added to the reaction mixture and the resulting solution was stirred for 2 hours. To the resulting mixture was added 100 ml. of cold water. The layers were separated and the organic layer was washed with water, dried over magnesium sulfate and concentrated in vacuo to yield a crude product. The crude product was distilled at 128° C. (0.03 mmHg) to yield 2'-[(2ethoxy)ethoxy]-6'-isopropyl-N-(ethoxy)methyl-2-chloroacetanilide (4.4 g; 80% yield) as a yellow liquid; b.p., 128° C. @ 0.03 mmHg.

Anal. Calc'd. for $C_{18}H_{31}ClNO_4$: C, 60.41; H, 7.89; Cl, 9.91; Found: C, 60.36; H, 7.91; Cl, 9.92.

In a similar fashion other compounds were prepared. The data for said compounds is summarized in Table II below.

TABLE II

Reaction scheme: $X_1-CH_2-C(=O)-N(CH_2OR)-Ar(R_2)(R_3) + ROH + HCHO \xrightarrow{\text{Solvent, Acid Halide, PTC, Excess Base}} X_1-CH_2-C(=O)-N(CH_2OR)-Ar(R_2)(R_3)$

| Example Number | $R_2$ | $R_3$ | R | $X_1$ | b.p. (C.°) | Element | Calc'd | Found |
|---|---|---|---|---|---|---|---|---|
| 21 | $-O-(CH_2)_2-OCH_3$ | $-CH(CH_3)_2$ | $-CH_2CH_2CH_3$ | $-Br$ | 125° C. @ 0.03 mmHg | C | 60.41 | 60.39 |
| | | | | | | H | 7.89 | 7.90 |
| | | | | | | Cl | 9.91 | 9.94 |
| 22 | $-O-(CH_2)_2-OCH_3$ | $-CH_2CH_3$ | $-CH_2CH_3$ | $-Br$ | 125° C. @ 0.03 mmHg | C | 58.27 | 58.30 |
| | | | | | | H | 7.33 | 7.39 |
| | | | | | | Cl | 10.75 | 10.76 |
| 23 | $-O-(CH_2)_2-OCH_3$ | $-CH_2CH_3$ | $-CH(CH_3)_2$ | $-Br$ | 127° C. @ 0.04 mmHg | C | 59.38 | 59.39 |
| | | | | | | H | 7.62 | 7.63 |
| | | | | | | Cl | 10.31 | 10.29 |
| 24 | $-O-(CH_2)_2-OCH_3$ | $-CH_2CH_3$ | $-CH_2CH_2CH_3$ | $-Br$ | 125° C. @ 0.03 mmHg | C | 59.38 | 59.40 |
| | | | | | | H | 7.62 | 7.63 |
| | | | | | | Cl | 10.31 | 10.30 |
| 25 | $-O-(CH_2)_2-OCH_2CH_3$ | $-H$ | $-CH_2CH_2CH_3$ | $-Cl$ | 124° C. @ 0.03 mmHg | C | 58.27 | 58.31 |
| | | | | | | H | 7.33 | 7.36 |
| | | | | | | Cl | 10.75 | 10.70 |
| 26 | $-O-(CH_2)_2-OCH_2CH_3$ | $-H$ | $-CH_2CH(CH_3)_2$ | $-Cl$ | 131° C. @ 0.02 mmHg | C | 59.38 | 59.32 |
| | | | | | | H | 7.62 | 7.60 |
| | | | | | | Cl | 10.31 | 10.32 |
| 27 | $-O-(CH_2)_2-OCH_2CH(CH_3)_2$ | $-CH_3$ | $-CH_2CH_3$ | $-Cl$ | 126° C. @ 0.03 mmHg | C | 60.41 | 60.31 |
| | | | | | | H | 7.89 | 7.89 |
| | | | | | | Cl | 9.91 | 9.89 |
| 28 | $-O-(CH_2)_2-OCH_2CH(CH_3)_2$ | $-CH_3$ | $-CH_2CH_2Cl$ | $-Cl$ | 162° C. @ 0.03 mmHg | C | 55.11 | 55.02 |
| | | | | | | H | 6.94 | 6.97 |
| | | | | | | Cl | 18.07 | 18.01 |
| 29 | $-O-(CH_2)_2-OCH_2CH(CH_3)_2$ | $-CH_3$ | $-CH_2CH_2CH_3$ | $-Cl$ | 143° C. @ 0.03 mmHg | C | 61.36 | 61.47 |
| | | | | | | H | 8.13 | 8.15 |
| | | | | | | Cl | 9.53 | 9.51 |
| 30 | $-O-CH_2-O-(CH_2)_2-OCH_3$ | $-H$ | $-CH_2CH_3$ | $-Cl$ | 145° C. @ 0.06 mmHg | C | 54.30 | 54.31 |
| | | | | | | H | 6.68 | 6.67 |

TABLE II-continued

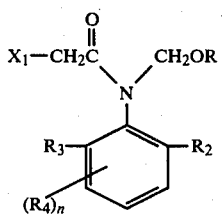

| Example Number | $R_2$ | $R_3$ | R | $X_1$ | b.p. (C.°) | Element | Calc'd | Found |
|---|---|---|---|---|---|---|---|---|
| 31 | $-O-CH_2-O-(CH_2)_2-OCH_3$ | $-H$ | $-CH_3$ | $-Cl$ | 140° C. @ 0.07 mmHg | Cl<br>C<br>H | 10.69<br>52.92<br>6.34 | 10.63<br>52.90<br>6.34 |
| 32 | $-O-(CH_2)_2-O-(CH_2)_2-OCH_3$ | $-CH_3$ | $-CH_2CH_3$ | $-Cl$ | 160° C. @ 0.08 mmHg | Cl<br>C<br>H | 11.16<br>56.71<br>7.28 | 11.15<br>56.81<br>7.32 |
| 33 | $-O-(CH_2)_2-OCH_2CH_3$ | $-CH(CH_3)_2$ | $-CH(CH_3)_2$ | $-Cl$ | 125° C. @ 0.05 mmHg | Cl<br>C<br>H<br>Cl | 9.85<br>61.36<br>8.13<br>9.53 | 9.88<br>61.28<br>8.17<br>9.52 |

What is claimed is:

1. A process for preparing a compound of the formula

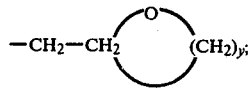
(IV)

where $X_1$ is chloro, bromo or iodo; R is $C_{1-10}$ alkyl, $C_{3-10}$ alkenyl, $C_{3-10}$ cycloalkyl, $C_{3-10}$ alkynyl, $C_{1-5}$ alkoxy $(C_{2-5})$ alkyl, mono-halo $(C_{2-5})$ alkyl, mono-halo $(C_{3-5})$ alkenyl or

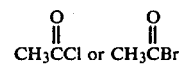

y is the integer 2, 3 or 4; with the proviso that when R is alkenyl or alkynyl the carbon atom attached to the oxygen may not share a double or triple bond with an adjacient carbon atom;

$R_2$ is $C_{1-8}$ alkyl, $C_{2-8}$ alkenyl, $C_{3-8}$ alkynyl, $C_{1-8}$ alkoxy, $C_{1-8}$ alkoxy $(C_{1-5})$ alkyl, halo $(C_{1-5})$ alkyl, halogen, $NO_2$, $C_{1-5}$ alkoxy $(C_{1-5})$ alkoxy or $C_{1-5}$ alkalkoxy $(C_{1-5})$ alkoxy $(C_{1-5})$ alkoxy; $R_3$ is hydrogen, $C_{1-8}$ alkyl, $C_{2-8}$ alkenyl, $C_{1-8}$ alkoxy, $C_{1-8}$ alkoxy $(C_{1-5})$ alkyl, halo $(C_{1-5})$ alkyl, halogen or $NO_2$;

$R_4$ is $C_{1-8}$ alkyl, halo $(C_{1-5})$ alkyl, halogen or $NO_2$; n is the integer zero, one or two;

which comprises reacting, in a solvent and in the presence of a phase transfer catalyst, an alcohol of the formula

ROH  (V)

(where R is as defined in Formula IV);
formaldehyde, an acid halide and a compound of the formula

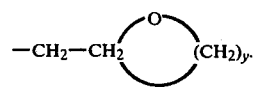
(VI)

(where $X_1$, $R_1$, $R_3$, $R_4$ and n are as defined in Formula IV); followed by addition of excess base.

2. A process according to claim 1 wherein said acid halide is HCl, HBr, HI, $$\overset{O}{\underset{}{\|}}\quad \overset{O}{\underset{}{\|}}$$
$$CH_3CCl \text{ or } CH_3CBr$$

and wherein said base is NaOH or KOH.

3. A process according to claim 1 wherein $X_1$ is chloro.

4. A process according to claim 1 wherein R is $C_{1-10}$ alkyl, $C_{3-10}$ cycloalkyl, $C_{1-5}$ alkoxy $(C_{2-5})$ alkyl, mono-halo$(C_{2-5})$ alkyl or $$-CH_2-CH_2\underset{}{\overset{O}{\frown}}(CH_2)_y.$$

5. A process according to claim 1 wherein R is $C_{3-10}$ alkynyl or mono-halo$(C_{3-5})$ alkenyl.

6. A process according to claim 1 wherein $R_2$ is $C_{1-8}$ alkoxy $(C_{1-5})$ alkyl, halo $(C_{1-5})$ alkyl, $NO_2$, $C_{1-5}$ alkoxy $(C_{1-5})$ alkoxy or $C_{1-5}$ alkoxy $(C_{1-5})$ alkoxy $(C_{1-5})$ alkoxy.

7. A process according to claim 6 wherein $R_2$ is trifluoromethyl.

8. A process according to claim 1 wherein $R_3$ is hydrogen, $C_{1-8}$ alkyl, $C_{1-8}$ alkoxy, $C_{1-8}$ alkoxy $(C_{1-5})$ alkyl, or halo $(C_{1-5})$ alkyl.

9. A process according to claim 1 wherein n is zero.

10. A process according to claim 1 wherein n is one.

11. A process according to claim 1 wherein said solvent is methylene chloride.

12. A process according to claim 1 wherein the temperature of the reaction is from about 10° to about 50° C.

* * * * *